United States Patent
Verner et al.

(10) Patent No.: US 11,376,087 B2
(45) Date of Patent: Jul. 5, 2022

(54) UNIFORM SCALING OF HAPTIC ACTUATORS

(71) Applicant: Intuitive Surgical Operations, Inc., Sunnyvale, CA (US)

(72) Inventors: Lawton N. Verner, San Jose, CA (US); Hsien-Hsin Liao, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 59 days.

(21) Appl. No.: 16/069,810

(22) PCT Filed: Jan. 12, 2017

(86) PCT No.: PCT/US2017/013239
§ 371 (c)(1),
(2) Date: Jul. 12, 2018

(87) PCT Pub. No.: WO2017/123797
PCT Pub. Date: Jul. 20, 2017

(65) Prior Publication Data
US 2019/0015169 A1  Jan. 17, 2019

Related U.S. Application Data

(60) Provisional application No. 62/277,827, filed on Jan. 12, 2016.

(51) Int. Cl.
*A61B 34/00* (2016.01)
*A61B 34/30* (2016.01)
*A61B 90/00* (2016.01)

(52) U.S. Cl.
CPC ............. *A61B 34/76* (2016.02); *A61B 34/30* (2016.02); *A61B 34/77* (2016.02); *A61B 2090/064* (2016.02)

(58) Field of Classification Search
CPC ......... A61B 34/76; A61B 34/30; A61B 34/77; A61B 2090/064
(Continued)

(56) References Cited

U.S. PATENT DOCUMENTS 4,604,016 A * 8/1986 Joyce ..................... B25J 13/02
414/5
5,116,180 A * 5/1992 Fung ..................... B25J 9/1689
414/5
(Continued)

FOREIGN PATENT DOCUMENTS

CN  101443162 A  5/2009
CN  102612350 A  7/2012
(Continued)

OTHER PUBLICATIONS

International Search Report and Written Opinion for Application No. PCT/US2017/013239, dated May 1, 2017, 9 pages.
(Continued)

*Primary Examiner* — Carl H Layno
*Assistant Examiner* — Michael J Lau

(57) ABSTRACT

A surgical system is provided comprising: an input device; a first actuator and a second actuator; a controller for controlling the first actuator and the second actuator, the controller configured to apply a first scale factor to a first commanded output and a second commanded output for the first actuator the second actuator, respectively, when the first commanded output would fall outside a first predetermined working range of the first actuator, wherein the first scale factor adjusts the first commanded output to be within the first predetermined working range.

27 Claims, 4 Drawing Sheets

(58) Field of Classification Search
USPC .......................................................... 606/1
See application file for complete search history.

(56) References Cited

U.S. PATENT DOCUMENTS

| | | | | |
|---|---|---|---|---|
| 5,382,885 | A * | 1/1995 | Salcudean | B25J 3/04 318/568.1 |
| 5,696,837 | A | 12/1997 | Green | |
| 6,024,576 | A | 2/2000 | Bevirt et al. | |
| 6,102,850 | A | 8/2000 | Wang et al. | |
| 6,459,926 | B1 | 10/2002 | Nowlin et al. | |
| 6,594,552 | B1 | 7/2003 | Nowlin et al. | |
| 6,639,581 | B1 * | 10/2003 | Moore | G05G 9/047 345/156 |
| 6,723,106 | B1 * | 4/2004 | Charles | B25J 9/1065 606/130 |
| 6,994,703 | B2 | 2/2006 | Wang et al. | |
| 7,373,219 | B2 | 5/2008 | Nowlin et al. | |
| 7,843,158 | B2 * | 11/2010 | Prisco | A61B 34/71 318/566 |
| 8,390,218 | B2 | 3/2013 | Houston et al. | |
| 8,644,988 | B2 | 2/2014 | Prisco et al. | |
| 9,173,713 | B2 | 11/2015 | Hart et al. | |
| 9,198,714 | B2 | 12/2015 | Worrell et al. | |
| 2002/0120188 | A1 * | 8/2002 | Brock | A61B 5/0086 600/407 |
| 2004/0024311 | A1 * | 2/2004 | Quaid, III | A61B 34/10 600/428 |
| 2004/0106916 | A1 * | 6/2004 | Quaid | A61B 34/76 606/1 |
| 2004/0243147 | A1 * | 12/2004 | Lipow | A61B 34/35 606/130 |
| 2006/0149418 | A1 * | 7/2006 | Anvari | A61G 13/10 700/245 |
| 2006/0207978 | A1 | 9/2006 | Rizun et al. | |
| 2007/0142968 | A1 | 6/2007 | Prisco et al. | |
| 2007/0239028 | A1 | 10/2007 | Houser | |
| 2009/0062813 | A1 | 3/2009 | Prisco et al. | |
| 2009/0248037 | A1 * | 10/2009 | Prisco | A61B 34/71 606/130 |
| 2009/0248038 | A1 | 10/2009 | Blumenkranz | |
| 2010/0073150 | A1 * | 3/2010 | Olson | A61B 34/74 340/407.1 |
| 2010/0256558 | A1 * | 10/2010 | Olson | A61B 34/20 604/95.01 |
| 2010/0274087 | A1 | 10/2010 | Diolaiti et al. | |
| 2010/0275718 | A1 * | 11/2010 | Stuart | A61B 34/77 74/490.01 |
| 2011/0040306 | A1 * | 2/2011 | Prisco | A61B 34/71 606/130 |
| 2011/0295247 | A1 | 12/2011 | Schlesinger et al. | |
| 2012/0078080 | A1 * | 3/2012 | Foley | A61B 34/30 600/411 |
| 2012/0116391 | A1 | 5/2012 | Houser et al. | |
| 2012/0184955 | A1 * | 7/2012 | Pivotto | A61B 34/74 606/41 |
| 2012/0265051 | A1 * | 10/2012 | Fischer | A61B 90/11 600/411 |
| 2013/0103050 | A1 | 4/2013 | Richmond et al. | |
| 2013/0131867 | A1 | 5/2013 | Olds et al. | |
| 2013/0172906 | A1 * | 7/2013 | Olson | A61B 34/74 606/130 |
| 2013/0211418 | A1 | 8/2013 | Lim et al. | |
| 2013/0211590 | A1 | 8/2013 | Diolaiti et al. | |
| 2013/0289767 | A1 * | 10/2013 | Lim | A61B 34/76 700/253 |
| 2013/0304258 | A1 * | 11/2013 | Taylor | A61B 34/30 700/260 |
| 2014/0081460 | A1 * | 3/2014 | Ando | B25J 9/1641 700/260 |
| 2014/0142592 | A1 * | 5/2014 | Moon | A61B 34/37 606/130 |
| 2015/0045812 | A1 * | 2/2015 | Seo | A61B 34/30 606/130 |
| 2015/0245876 | A1 * | 9/2015 | Kim | G06F 3/0338 700/264 |
| 2015/0360365 | A1 * | 12/2015 | Fudaba | A61B 34/76 700/254 |

FOREIGN PATENT DOCUMENTS

| | | |
|---|---|---|
| CN | 103203755 A | 7/2013 |
| CN | 203092570 U | 7/2013 |
| JP | 2012513845 A | 6/2012 |
| WO | WO-2006120666 A1 | 11/2006 |
| WO | WO-2013164622 A1 | 11/2013 |
| WO | WO2017/146890 A1 | 8/2017 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP17738964.0 dated Aug. 16, 2019, 9 pages.

Extended European Search Report for Application No. EP21153588.5 dated Jul. 9, 2021, 7 pages.

* cited by examiner

UNIFORM SCALING OF HAPTIC ACTUATORS

CLAIM OF PRIORITY

This application is a U.S. National Stage Filing under 35 U.S.C. 371 from International Application No. PCT/US2017/013239, filed on Jan. 12, 2017, and published as WO 2017/123797 A1 on Jul. 20, 2017, which claims the benefit of priority to U.S. Provisional Patent Application No. 62/277,827, filed on Jan. 12, 2016, each of which is hereby incorporated by reference herein in its entirety.

FIELD

The present invention is directed towards systems and methods for providing haptic feedback to the operator of a surgical system, and more particularly to maintaining an intuitive haptic profile for the user when haptic feedback actuators reach performance limits.

BACKGROUND

Tele-operated surgical systems are often intended to enhance surgeon precision and/or reduce patient trauma during a medical procedure. In such systems, a surgeon interacts with input devices (sometimes referred to as "masters" or "master controllers") to control surgical instruments that are actuated by drive mechanisms such as motors. Because the surgeon is not directly manipulating the surgical instruments, in can sometimes be beneficial to provide haptic feedback at the input devices that indicates or replicates interaction forces (e.g., felt at the surgical instruments, other elements of the surgical system, and/or virtual or synthetic elements/features generated by the surgical system). Note that the force feedback being presented to the user may be the sum of the feedback from a sensor, from an algorithm, from a user interface cue, collision detection, model interaction, etc.

To provide a good user experience, the surgeon would ideally experience a seamless haptic experience through system state and configuration changes. However, this can be difficult to accomplish, for example the actuators used to provide the haptic feedback are have different performance limits or if different actuators reach their performance limits at different times. In such instances, the haptic feedback presented to the user may not properly align with the perceived user experience (e.g., actual force being sensed at the surgical instrument or the visual representation of the interactive object), resulting in a confusing or non-intuitive user experience.

For example, motor torque limits (i.e. saturation limits) are typically imposed in software for robotic interfaces. These performance limits can be created for several reasons including to protect the motor from overheating, to limit the force applied to the surgeon/patient, and/or to keep the motor in it's ideal torque operating range. Limiting the torque at the motor can yield non-isotropic force saturation at the interface (e.g., the handle of the input device or the tip of the instrument). This means when you are trying to present a force at the interface that involves two or more motors, the force direction can be incorrect if one motor is restricted by a motor torque limit.

This can be especially problematic when rendering force to the user (haptic feedback) at the input device. The user may be feeling a force in a given direction, but as the force applied to the user increases and reaches a torque limit for any of the motors associated with render the force to the user, the direction of the force displayed to the user begins to rotate which can be disconcerting and/or confusing for the user.

It is therefore desirable to provide a system and method for ensuring haptic feedback that is consistent with the force environment at the surgical instrument.

SUMMARY

To minimize discrepancies between expected force directions and haptic force feedback directions, the outputs of the haptic feedback actuators are scaled whenever one or more of the actuators reaches a predetermined output threshold, thereby maintaining proper haptic feedback directionality when individual actuators would otherwise be commanded to operate outside their accurate performance range. Such scaling may change the overall haptic feedback magnitude, but allows the haptic feedback direction to be appropriately maintained.

In some embodiments, where software limits the output of any actuator, a monitoring process can determine when an output of an actuator would exceed a maximum threshold output (at or below the software-defined output limit), and at that point scale down the output of at least one of the other actuators so that the desired direction of the total output (e.g., force or torque) is maintained. In some embodiments, the monitoring process can additionally or alternatively determine when an output of an actuator would fall below a minimum output threshold (below which the actuator output may be too low to generate accurately), and at that point scale up its output and that of at least one of the other actuators so that the desired direction of the total output (e.g., force or torque) is maintained. In some embodiments, all actuators are scaled when one reaches its threshold output, while in other embodiments, only concurrently active actuators are scaled. In some embodiments, the output thresholds for the actuators are fixed, and in various other embodiments, the output thresholds for the actuators can vary over time or based on actuator and/or system status.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

To minimize discrepancies between desired (e.g., sensed or modeled by a surgical system) and actual haptic force feedback directions, the outputs of the haptic feedback actuators are scaled whenever a commanded output of one or more of the actuators falls outside a predetermined working range for that actuator. The predetermined working range can be defined by a maximum output threshold equal to or less than the output limit of the actuator, and/or a minimum output threshold equal to or greater than a minimum accurate output level of the actuator. Such scaling may reduce the overall haptic feedback magnitude, but allows the haptic feedback direction to be appropriately maintained, which is often a more critical aspect of haptic feedback.

Figure 1:
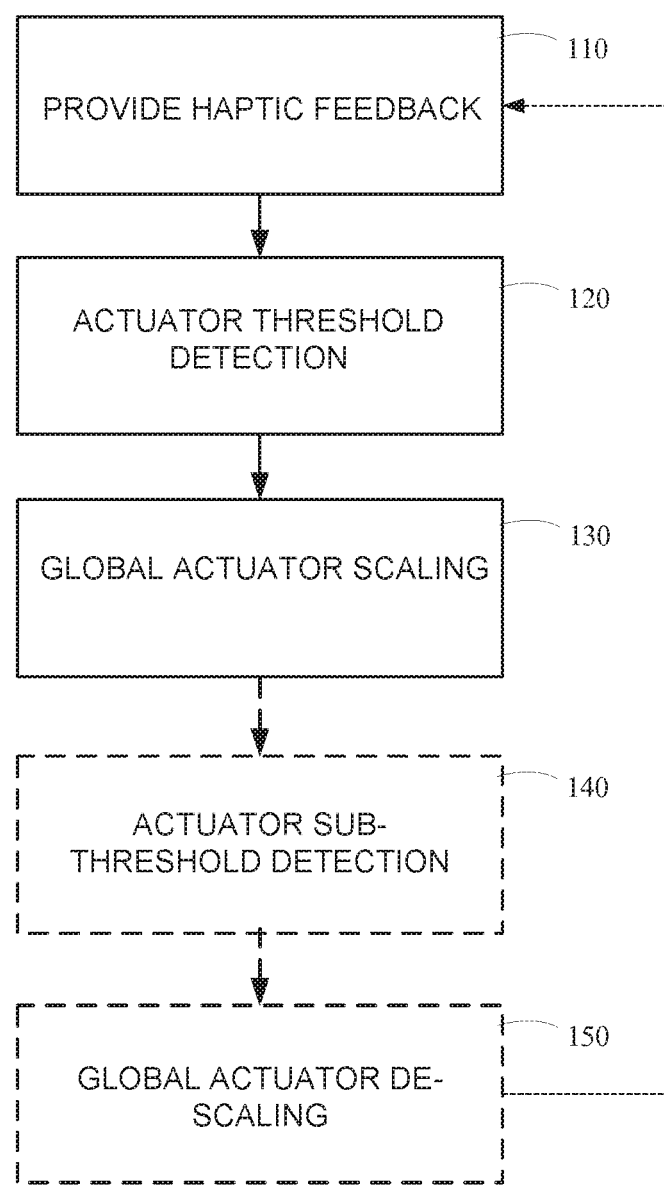
FIG. 1 shows a method of providing consistent haptic feedback to a user of a surgical system as actuator maximum outputs are reached, in accordance with various embodiments of the invention.

FIG. 1 shows an exemplary method for providing directionally consistent haptic feedback when actuator output limits are exceeded. In a PROVIDE HAPTIC FEEDBACK step 110, a surgical system that allows a user (e.g., surgeon) to control a surgical instrument (and/or other elements of the surgical system, such as a robotic arm, set up structure, or positioning element such as a boom or cart) via an input device(s) (e.g., lever(s), gripper(s), joystick(s), or any other structure capable of receiving user input), and then provides force feedback to that input device based on a desired haptic feedback profile (a set of one or more haptic feedback effects that at least partially reproduce or represent the physical experience of a real or virtual/modeled interaction). The haptic feedback profile can be based on any haptic model input, such as sensed forces at the instrument (e.g., tissue or other instrument interactions) or robotic arm (e.g., arm collisions with structures or staff), user guidance (e.g., haptic detents, fences, or other profiles to provide guidance for the user to move the input device(s) along a desired path or trajectory), and user interface (UI) elements (e.g., presenting a virtual handle or steering wheel to the user). This haptic feedback can be anything from direct replication of the haptic feedback profile, to scaling of the haptic feedback profile, to applying a non-linear modification of the haptic feedback profile, or any other transformation (e.g., force scaling that varies depending on one or more other factors such as instrument state/speed, viewing magnification, etc.).

The actual force feedback provided at the input device is generated by two or more actuators (e.g., motors, drives, or any other motive elements) that work cooperatively to provide feedback of varying force and direction. For example, an input device having pitch and yaw capabilities may be coupled to a first pair of actuators that apply forces in opposing directions about the pitch axis, and a second pair of actuators that apply forces in opposing directions about the yaw axis. Two or more of the pitch and yaw actuators can then be used simultaneously to provide force feedback that is offset from the pitch and yaw axes.

Because actuators generally do not have performance characteristics that are exactly the same, whether due to inherent performance limitations or due to operational constraints/effects (e.g., heat, mechanical restrictions). For example, one out of the group of haptic feedback actuators will typically reach its maximum output level before the others. Any commanded output beyond that maximum output level will not result in any increased output, and consequently any haptic feedback that involves the maxed-out actuator will likely deviate from the expected force feedback direction. Additionally, the actuators will may begin producing noisier (less precise) outputs as outputs decrease below a certain level, such that haptic feedback below a certain level may also deviate from the expected force feedback direction.

Figure 2A:
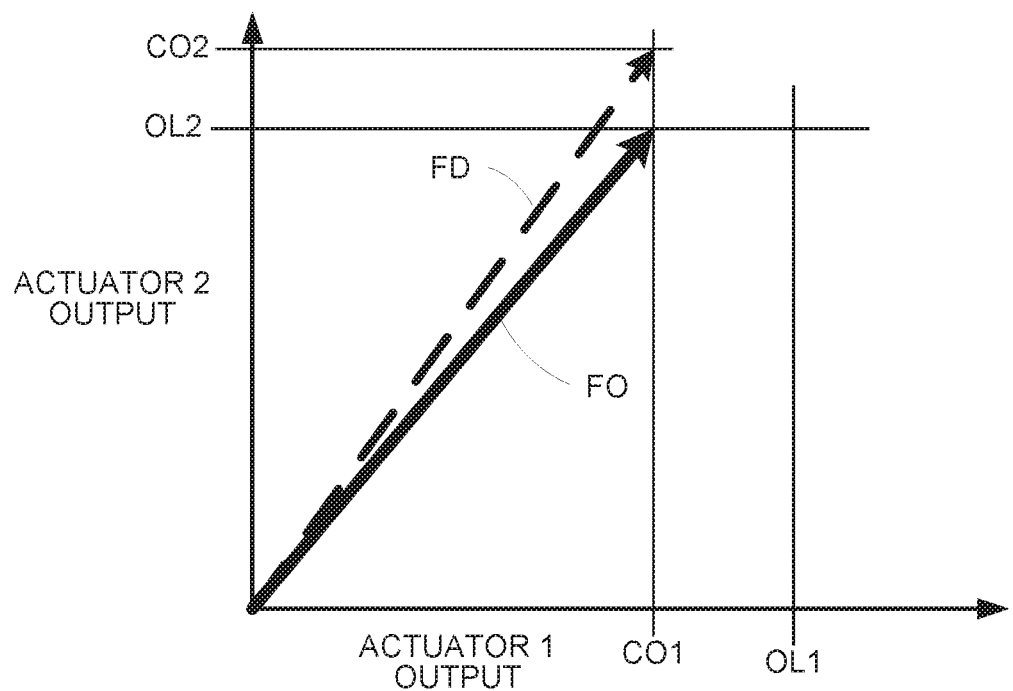
FIGS. 2A and 2B shows an exemplary haptic force vector outputs when actuator output maximums are ignored vs. addressed.

FIG. 2A graphically depicts an example of this haptic offset, with the outputs of first and second actuators ("Actuator 1" and "Actuator 2", respectively) represented by the graph's horizontal and vertical axes, respectively. Also indicated on the axes of the graph are output limits OL1 and OL2 for the first and second actuators, respectively, representing the output limits for the first and second actuators.

As noted above, the actuators cannot exceed their output limits, which may be static (e.g., defined by inherent performance characteristics of the actuators), or dynamic (e.g., based on a current parameter of an actuator, such as temperature, or a physical restriction such as a kinematic configuration of the driven structure that places the actuator in a mechanically unfavorable position).

The problem thus arises if a commanded output of an actuator exceeds its output limit, such as indicated by desired (commanded) feedback force FD. To generate desired feedback force FD, actuator 1 receives a commanded output CO1, and actuator 2 receives a commanded output CO2. Commanded output CO1 is less than output limit OL1, and so can be provided by actuator 1. However, because commanded output CO2 is greater than output limit OL2, the actual output of actuator 2 will be limited to output level OL2, resulting in an overall feedback force FO that is both smaller than, and offset from, desired feedback force FD. While a slight variability in the magnitude of haptic feedback can generally be accommodated by a user without much difficulty, a deviation in force direction can be quite misleading to a user and can result in improper control actions by the user in response.

Returning to FIG. 1, to mitigate this force feedback offset issue, in an ACTUATOR THRESHOLD DETECTION step 120, any commanded output for an actuator that exceeds a maximum output threshold for that actuator is identified. Note that while in some embodiments the maximum output threshold for an actuator can be defined as the output limit for that actuator, in various other embodiments the maximum output threshold could be set at a level below the output limit to provide a buffer for detecting the approach of the actuator limit and/or applying the scaling factor (as described in greater detail below) before any output limits are reached. Note further that as described above, the maximum output thresholds for the haptic feedback actuators can be either static or dynamic, and can be individualized or common across the actuators.

Then, in a GLOBAL ACTUATOR SCALING step 130, a common scaling factor is applied to the commanded outputs for the actuators. The scaling factor is selected to keep the output of the identified actuator (i.e., the actuator identified in step 120 having a commanded output greater than its output threshold) less than its output limit. Because the scaling factor is applied to the commanded output for each actuator, the direction of the overall force is maintained, with a reduced overall magnitude. Note that in some embodiments, if multiple actuators would receive commanded outputs that would exceed their output limits, the scaling factor would be based on the commanded output that exceeds its associated actuator's output threshold by the greatest amount—i.e., the scaling factor would be based on the "worst" output discrepancy.

Figure 2B:
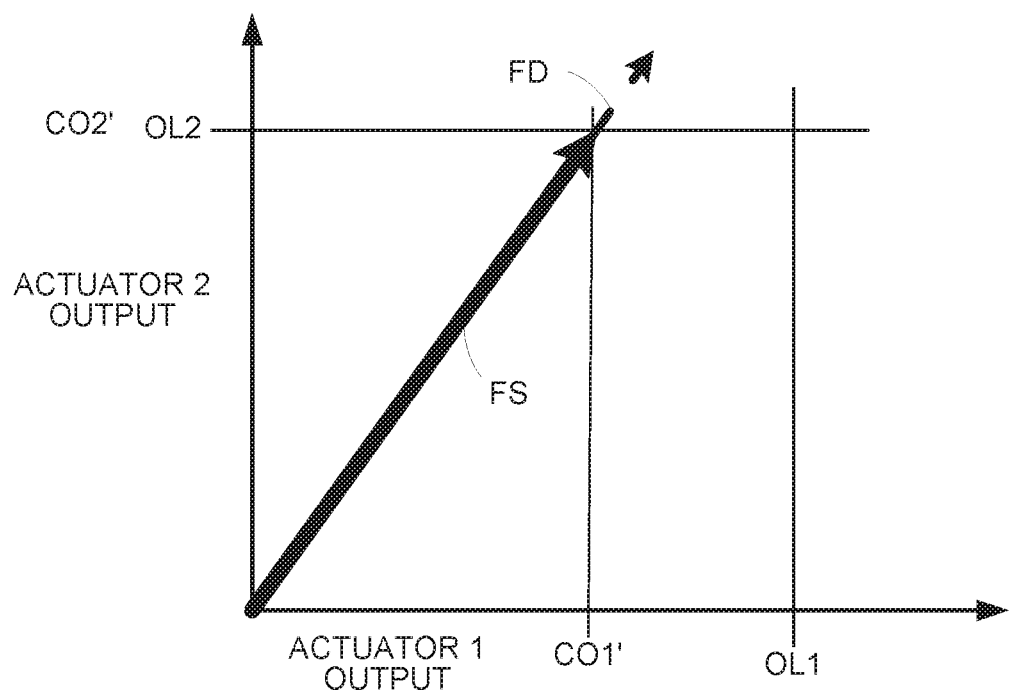

FIG. 2B graphically depicts an example of this haptic scaling, relative to the same first and second actuator characteristics (output limits OL1 and OL2, respectively) and desired feedback force FD. However, rather than allowing the output limits associated with actuator 2 to pull the overall haptic force off the desired force direction as shown in FIG. 2A, a scaling factor is applied to the commanded outputs CO1 and CO2 to reduce both proportionately to adjusted commanded outputs CO1' and CO2', respectively. The scaling factor is selected such that adjusted commanded output CO2' reduced at least to output limit OL2, although in various other embodiments the scaling factor can be selected to cause adjusted commanded output CO2' to be some increment less than output limit OL2.

In some embodiments, actuators 1 and 2 could additionally or alternatively exhibit reduced output accuracy at low output levels. In such embodiments, a scaling factor could be applied to commanded outputs CO1 and CO2 if either is less than a minimum output threshold for actuator 1 or actuator 2, respectively. The scaling factor would then increase the adjusted commanded outputs CO1' and CO2' above the level at which output accuracy is degraded. Note that as described above, the minimum output thresholds for the haptic feedback actuators can be either static or dynamic, and can be individualized or common across the actuators.

In any event, the application of the scaling factor results in an overall scaled feedback force FS that is aligned directionally with the original desired feedback force FD. As noted above, a consistent haptic experience can be provided even with the change in force magnitude so long as directional consistency of the force feedback is maintained.

Returning to FIG. 1, in various embodiments, when it is detected that the commanded output (unscaled) for the actuator identified in step 120 would go beyond the output threshold (e.g., exceed the maximum output threshold or fall below the minimum output threshold) for that actuator in an optional ACTUATOR SUB-THRESHOLD DETECTION step 140, the scaling factor applied to all commanded outputs in step 130 is removed (or set to 1) in an optional GLOBAL ACTUATOR DE-SCALING step 150. Returning to step 110, unscaled haptic feedback is provided going forward.

As noted previously, in some embodiments, the output thresholds for the haptic feedback actuators can be dynamic—i.e., the specific values can change depending on actuator operational parameters, input device kinematic configuration, or various other factors. In such embodiments, over the course of operation of the surgical system, the output threshold(s) applied in step 120 can have different values. In addition, in various other embodiments, different actuators can trigger step 120 over the course of operation of the surgical system.

Figure 3A:
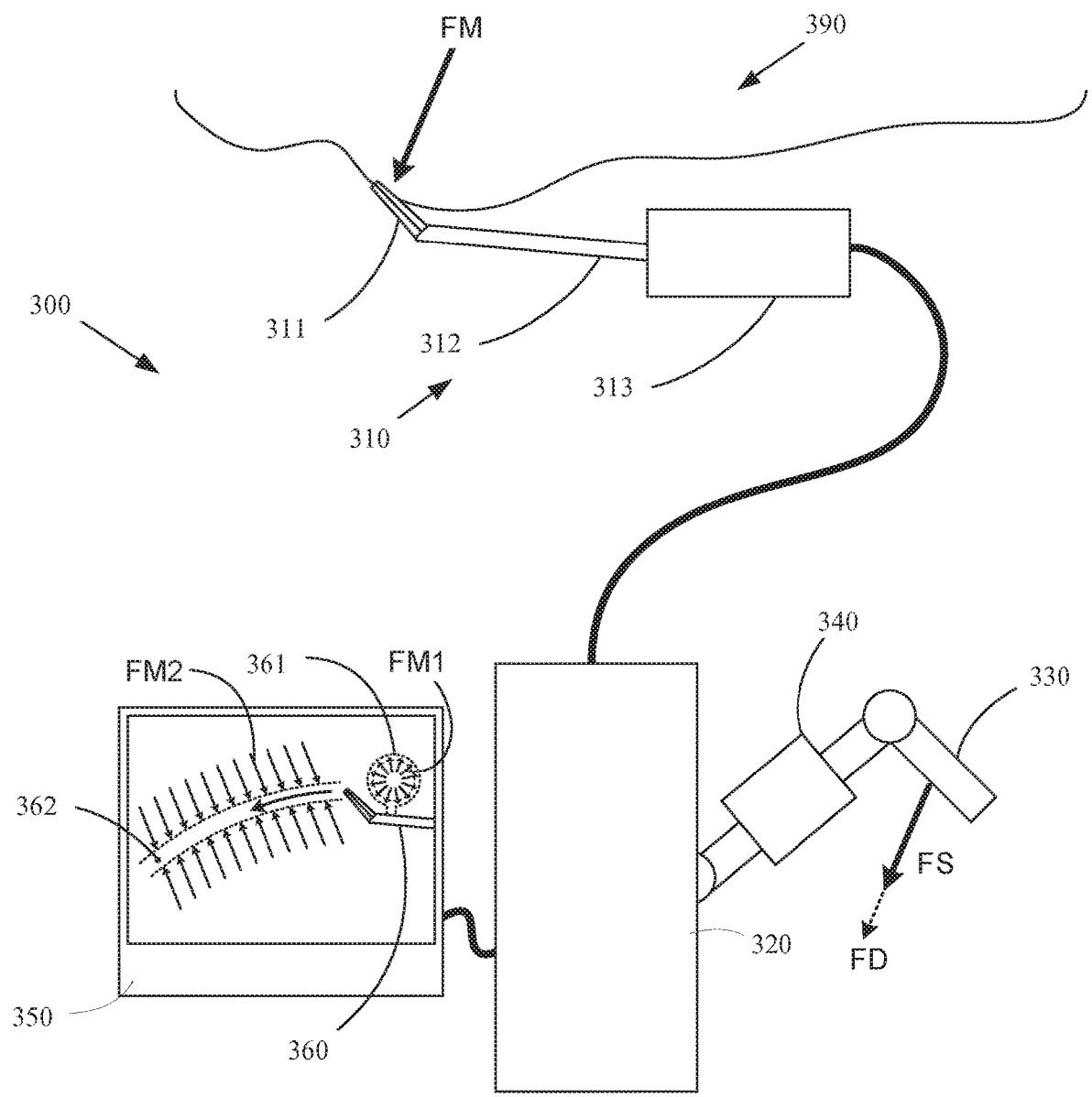
FIG. 3A-3B show an exemplary surgical system providing haptic force feedback responsive to actuator output maximum thresholds, in accordance with various embodiments of the invention.
Figure 3B:
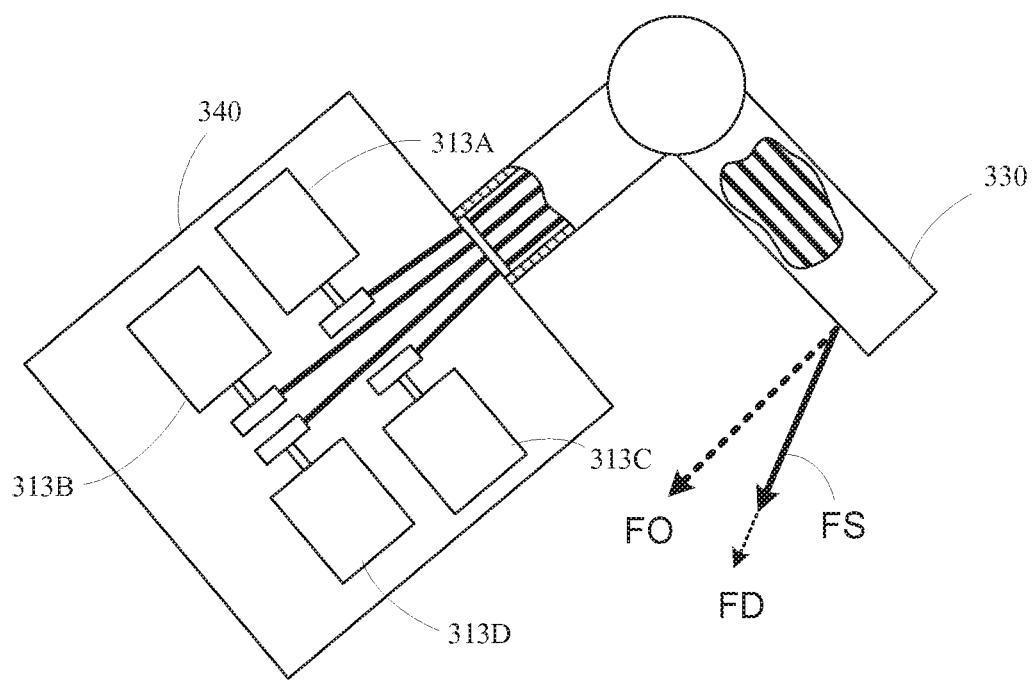

FIGS. 3A and 3B shows block diagram of a surgical system 300 incorporating haptic feedback at an input device 330 and means for providing a consistent haptic experience for the user as described above with respect to FIGS. 1, 2A, and 2B. Surgical system 300 includes an instrument 310 for performing a surgical task (e.g., forceps, cutter, retractor, vessel sealer, needle driver, catheter, etc.), an input device 330 (e.g., a lever(s), gripper(s), joystick(s), or any other structure capable of receiving user input) for receiving inputs from a user (e.g., surgeon), and a controller 320 for receiving input instructions from input device 330, controlling the actions of instrument 310 accordingly via a manipulation structure 313, and providing instructions to a haptic feedback actuation mechanism 340 to provide haptic feedback to input device 330 according to a desired haptic feedback profile. In various embodiments, manipulation structure 313 can include any number of systems and structures for maneuvering, positioning, actuating, or otherwise controlling the behavior of instrument 310, including a robotic arm(s)/manipulator(s), set up structure(s), and/or positioning element(s) such as a boom(s) or cart(s), among others. Controller 320 can include any combination of hardware, software, firmware, and other modalities for generating, managing, controlling, and effecting the actions described herein. In various embodiments, controller 320 can be integrated with instrument 310, input device 330, and/or discrete control hardware (e.g., a standalone processing unit or computing platform).

For exemplary purposes, FIG. 3A shows an end effector 311 at the end of a shaft 312 of instrument 310 grasping a portion of tissue 390 (e.g., retraction). This results in a force FM at end effector 311, which would ideally be delivered as a desired haptic feedback profile force FD at input device 330. The actual haptic feedback delivery is enabled by haptic feedback actuation mechanism 340, which includes multiple actuators that attempt to provide the haptic feedback profile force FD to present the surgeon with a "feel" of the resistance being provided by tissue 390 as it is being retracted.

Although the haptic feedback profile force FD is described as being derived from a force FM sensed at end effector 311 of instrument 310 for exemplary purposes, in various other embodiments, force FM could be sensed at any location for which corresponding haptic feedback at input device 330 would be beneficial, such as interactions at shaft 312 or any other element of manipulation structure 313 (e.g., arm collisions with structures or staff).

In various other embodiments, force FM can be defined according to non-physical parameters, such as guidance or user interface features. For example, in some embodiments, surgical system 300 can include a display 350 (e.g., a monitor(s), a head-in viewer(s), projections, video glasses/helmet(s), and/or any other graphical presentation element). In various embodiments, display 350 can present a virtual or synthetic element 361 that can be interacted with via input device 330. In some embodiments, synthetic element 361 can be used as a supplemental interface for interacting with a physical component of surgical system 300. For example, as shown in FIG. 3A, synthetic element 361 can be a virtual handle or knob that can be "grasped" and dragged around using input device 330 to reposition instrument 310 at the surgical site. In other embodiments, synthetic element 361 can provide a purely virtual interaction element, such as a dial, toggle, lever, or any other structure for controlling surgical system 300. In any case, by generating a haptic feedback profile based on model forces FM1 associated with interacting with synthetic element 361 (e.g., radially outward resistive force produced with grasping a round knob), controller 320 can then attempt to provide an appropriate haptic feedback profile force FD at input device 330.

In various other embodiments, surgical system 300 may provide guidance to the user with respect to movement of instrument 310 and/or input device 330. For example, a desired motion of instrument 310 (e.g., a targeted or safe dissection path, a desired retraction movement, or any other beneficial articulation) could optionally be defined as a trajectory 362. By generating a haptic feedback profile based on model forces FM2 associated with maintaining the position of instrument 310 along trajectory 362 (e.g., inwardly directed forces produced upon deviations from trajectory 362), controller 320 can then attempt to provide an appropriate haptic feedback profile force FD at input device 330.

FIG. 3B shows an exemplary block diagram of actuation mechanism 340 that includes multiple actuators 341 that apply components of the haptic feedback force to input device 330. Note that while four actuators that drive input device 330 via cables or tendons are depicted for descriptive purposes, in various other embodiments, actuation mechanism 340 can include any number and type of actuators (e.g., rotary actuators, linear actuators, hydraulics, and/or piezoelectric, vibrotactile, or fluidic actuators) and/or force transmission mechanisms (e.g., direct drive, linkages, gearing, etc.).

The various actuators 341 provide actuation outputs (e.g., torque or force) in combination with one another in an effort to produce the desired haptic feedback profile force FD. However, if desired haptic feedback profile force FD requires an output from one of actuators 341 that falls outside its working range, attempting to use the commanded outputs for actuators 341 without modification would result in an unmodified haptic feedback force FO having both a magnitude and direction different than desired force FD (as described above with respect to FIGS. 1 and 2A). As described above, the working range of an actuator can be defined by a maximum output threshold (e.g., at or below the output limit of the actuator) and/or a minimum output threshold (e.g., at or above a minimum reliable output level of the actuator).

Therefore, when controller 320 detects that a commanded output for any of actuators 341 would go beyond that actuator's defined output threshold (as described above with respect to step 120 in FIG. 1), it applies a common scaling factor to the commanded outputs supplied to each actuator 341 such that the commanded outputs for all actuators 341 remain within their predetermined working range (as described above with respect to step 130 in FIG. 1). This has the effect of changing the output of all actuators 341 proportionately, which in turn results in a scaled haptic feedback force FS that, while different in magnitude with respect to the desired feedback force FD, remains directionally aligned with desired feedback force FD (as described above with respect to FIG. 2B).

In various embodiments, when controller 320 detects that the unsealed commanded outputs would no longer go beyond the defined output thresholds for any of actuators 341, the scaling factor can be eliminated (or set to 1), thereby allowing restoration of unsealed haptic feedback at input device 330 (as described above with respect to steps 140 and 150 in FIG. 1).

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A surgical system comprising:
an input device;
a first actuator coupled to the input device;
a second actuator coupled to the input device; and
a controller;
wherein the input device is capable of receiving input from a user and providing a haptic feedback force to the user;
wherein the first actuator has a maximum output threshold force and a minimum reliable output level force;
wherein a working range of the first actuator is defined by an upper limit at or below the maximum output threshold force of the first actuator and a lower limit at or above the minimum reliable output level force of the first actuator;
wherein the controller determines a first commanded output haptic feedback force for the first actuator to provide to the input device and a second commanded output haptic feedback force for the second actuator to provide to the input device;
wherein on a condition in which the first commanded output haptic feedback force would fall outside the working range of the first actuator, the controller applies a common first scaling factor to the first commanded output haptic feedback force for the first actuator to provide to the input device and to the second commanded output haptic feedback force for the second actuator to provide to the input device; and
wherein the first scaling factor adjusts the first commanded output haptic feedback force to be within the first predetermined output force working range.

2. The surgical system of claim 1, wherein:
the second actuator has a maximum output threshold force and a minimum reliable output level force;
a working range of the second actuator is defined by an upper limit at or below the maximum output threshold force of the second actuator and an output limit at or above the minimum reliable output level force of the second actuator; and
the first scaling factor adjusts the second commanded output haptic feedback force to be within the working range of the second actuator.

3. The surgical system of claim 2, wherein:
on a second condition in which the first commanded output haptic feedback force would fall within the working range of the first actuator, the controller removes the first scaling factor from the first commanded output haptic feedback force and the second commanded output haptic feedback force.

4. The surgical system of claim 2, wherein:
on a second condition in which the first scaling factor applied to the first commanded output haptic feedback force would cause the first actuator to output a force outside the first working range of the first actuator, the controller applies a second scaling factor to the first commanded output haptic feedback force and to the second commanded output haptic feedback force; and
the second scaling factor adjusts the first commanded output haptic feedback force to be within the first working range of the first actuator.

5. The surgical system of claim 2, wherein:
on a second condition in which the first scaling factor applied to the first commanded output haptic feedback force would cause the second actuator to output a force outside the second working range of the second actuator, the controller applies a second scaling factor to the first commanded output haptic feedback force and to the second commanded output haptic feedback force; and the second scaling factor adjusts the second commanded output haptic feedback force to be within the second working range of the second actuator.

6. The surgical system of claim 2, wherein:
on a second condition in which the first scaling factor applied to the first commanded output haptic feedback force would cause the first actuator to output a force outside the first working range of the first actuator, the controller applies a second scaling factor to the first commanded output haptic feedback force and to the second commanded output haptic feedback force; and
the second scaling factor adjusts the first commanded output haptic feedback force to be within the first working range of the first actuator.

7. The surgical system of claim 2, wherein:
on a second condition in which the first scaling factor applied to the first commanded output haptic feedback force would cause the second actuator to output a force outside the second working range of the second actuator, the controller applies a second scaling factor to the first commanded output haptic feedback force and to the second commanded output haptic feedback force; and
the second scaling factor adjusts the second commanded output haptic feedback force to be within the second working range of the second actuator.

8. The surgical system of claim 2, wherein:
the condition in which the first commanded output haptic feedback force would fall outside the first working range of the first actuator is a condition in which the first commanded output haptic feedback force would be larger than the upper output limit of the first working range of the first actuator.

9. The surgical system of claim 2, wherein:
the condition in which the first commanded output haptic feedback force would fall outside the first working range of the first actuator is a condition in which the first commanded output haptic feedback force would be smaller than the lower output limit of the first working range of the first actuator.

10. The surgical system of claim 2, wherein:
the maximum output threshold force of the first actuator, the minimum reliable output level force of the first actuator, or both the maximum output threshold force and the minimum reliable output level force of the first actuator are dynamic and based on a kinematic configuration of the input device.

11. The surgical system of claim 2, wherein:
the maximum output threshold force of the first actuator, the minimum reliable output level force of the first actuator, or both the maximum output threshold force and the minimum reliable output level force of the first actuator are dynamic and based on a current parameter of the first actuator.

12. The surgical system of claim 2, wherein:
the first commanded output haptic feedback force has a first direction; and
the second commanded output haptic feedback force has a second direction different from the first direction.

13. The surgical system of claim 1, wherein:
on a second condition in which the first commanded output haptic feedback force would fall within the working range of the first actuator, the controller removes the first scaling factor from the first commanded output haptic feedback force and the second commanded output haptic feedback force.

14. The surgical system of claim 1, wherein:
on a second condition in which the first scaling factor applied to the first commanded output haptic feedback force would cause the first actuator to output a force outside the first working range of the first actuator, the controller applies a second scaling factor to the first commanded output haptic feedback force and to the second commanded output haptic feedback force; and
the second scaling factor adjusts the first commanded output haptic feedback force to be within the first working range of the first actuator.

15. The surgical system of claim 1, wherein:
on a second condition in which the first scaling factor applied to the first commanded output haptic feedback force would cause the second actuator to output a force outside the second working range of the second actuator, the controller applies a second scaling factor to the first commanded output haptic feedback force and to the second commanded output haptic feedback force; and
the second scaling factor adjusts the second commanded output haptic feedback force to be within the second working range of the second actuator.

16. The surgical system of claim 1, wherein:
the condition in which the first commanded output haptic feedback force would fall outside the first working range of the first actuator is a condition in which the first commanded output haptic feedback force would be larger than the upper output limit of the first working range of the first actuator.

17. The surgical system of claim 1, wherein:
the condition in which the first commanded output haptic feedback force would fall outside the first working range of the first actuator is a condition in which the first commanded output haptic feedback force would be smaller than the lower output limit of the first working range of the first actuator.

18. The surgical system of claim 1, wherein:
the maximum output threshold force of the first actuator, the minimum reliable output level force of the first actuator, or both the maximum output threshold force and the minimum reliable output level force of the first actuator are dynamic and based on a kinematic configuration of the input device.

19. The surgical system of claim 1, wherein:
the maximum output threshold force of the first actuator, the minimum reliable output level force of the first actuator, or both the maximum output threshold force and the minimum reliable output level force of the first actuator are dynamic and based on a current parameter of the first actuator.

20. The surgical system of claim 1, wherein:
the first commanded output haptic feedback force has a first direction; and
the second commanded output haptic feedback force has a second direction different from the first direction.

21. The surgical system of claim 1, wherein:
the first scaling factor adjusts the first commanded output haptic feedback force and the second commanded output haptic feedback force proportionately.

22. A method for operating a surgical system comprising an input device, and a first actuator and a second actuator coupled to the input device, the method comprising:
- detecting that a first commanded output haptic feedback force for the first actuator would fall outside a first predetermined output force working range for the first actuator; and
- providing haptic feedback force at the input device by applying a first scale factor to the first commanded output haptic feedback force by the first actuator and by applying the first scale factor to a second commanded output haptic feedback force by the second actuator;
- wherein the first predetermined output force working range upper limit is equal to or lower than a maximum output force of the first actuator, and a first predetermined output force working range lower limit is greater than or equal to minimum reliable output force level of the first actuator;
- wherein the first scale factor causes the first commanded output haptic feedback force to fall within the first predetermined output force working range;
- wherein the second actuator has a second predetermined output force working range having a second predetermined output force working range upper limit equal to or lower than maximum output force of the second actuator and having a second predetermined output force working range lower limit greater than or equal to a minimum reliable output level of the second actuator; and
- wherein the second commanded output haptic feedback force adjusted by the first scale factor falls within the second predetermined output force working range.

23. The method of claim 22, wherein:
a third actuator is coupled to provide a third commanded output haptic feedback force to the input device; and
providing the haptic feedback force further comprises applying the first scale factor to the third commanded output haptic feedback force for the third actuator.

24. The method of claim 22, wherein:
the method further comprises changing the first scale factor to a second scale factor on a condition of detecting that the first commanded output haptic feedback force scaled by the first scale factor would fall outside the first predetermined working range; and
the second scale factor adjusts the first commanded output haptic feedback force to fall within the first predetermined output force working range.

25. The method of claim 22, wherein:
the method further comprises applying a second scale factor to the first commanded output haptic feedback force and the second commanded output on a condition of detecting that the second commanded output haptic feedback force scaled by the first scale factor would fall outside a second predetermined output force working range for the second actuator; and
the second scale factor adjusts the second commanded output haptic feedback force to fall within the second predetermined output force working range.

26. The method of claim 25, wherein:
the first predetermined output force working range is different from the second predetermined output force working range.

27. The method of claim 22, wherein:
the first scaling factor adjusts the first commanded output haptic feedback force and the second commanded output haptic feedback force proportionately.

* * * * *

UNITED STATES PATENT AND TRADEMARK OFFICE
CERTIFICATE OF CORRECTION

PATENT NO. : 11,376,087 B2
APPLICATION NO. : 16/069810
DATED : July 5, 2022
INVENTOR(S) : Lawton N. Verner and Hsien-Hsin Liao It is certified that error appears in the above-identified patent and that said Letters Patent is hereby corrected as shown below:

In the Claims

Column 8, Line 58 (Claim 4): the phrase "the first working range" should be – the working range –

Column 8, Lines 63-64 (Claim 4): the phrase "the first working range" should be – the working range –

Column 9, Line 2 (Claim 5): the phrase "the second working range" should be – the working range –

Column 9, Lines 8-9 (Claim 5): the phrase "the second working range" should be – the working range –

Column 9, Line 14 (Claim 6): the phrase "the first working range" should be – the working range –

Column 9, Lines 19-20 (Claim 6): the phrase "the first working range" should be – the working range –

Column 9, Line 25 (Claim 7): the phrase "the second working range" should be – the working range –

Column 9, Lines 31-32 (Claim 7): the phrase "the second working range" should be – the working range –

Column 9, Lines 35-36 (Claim 8): the phrase "the first working range" should be – the working range –

Column 9, Line 38 (Claim 8): the phrase "the upper output limit" should be – the upper limit –

Column 9, Lines 38-39 (Claim 8): the phrase "the first working range" should be – the working range –

Signed and Sealed this
Thirtieth Day of August, 2022

Katherine Kelly Vidal
*Director of the United States Patent and Trademark Office*

Column 9, Lines 42-43 (Claim 9): the phrase "the first working range" should be – the working range –

Column 9, Lines 45-46 (Claim 9): the phrase "the first working range" should be – the working range –

Column 10, Line 12 (Claim 14): the phrase "the first working range" should be – the working range –

Column 10, Lines 17-18 (Claim 14): the phrase "the first working range" should be – the working range –

Column 10, Line 23 (Claim 15): the phrase "the second working range" should be – the working range –

Column 10, Lines 29-30 (Claim 15): the phrase "the second working range" should be – the working range –

Column 10, Lines 33-34 (Claim 16): the phrase "the first working range" should be – the working range –

Column 10, Line 36 (Claim 16): the phrase "the upper output limit" should be – the upper limit –

Column 10, Lines 36-37 (Claim 16): the phrase "the first working range" should be – the working range –

Column 10, Lines 40-41 (Claim 17): the phrase "the first working range" should be – the working range –

Column 10, Lines 43-44 (Claim 17): the phrase "the first working range" should be – the working range –